(12) United States Patent
Plouët et al.

(10) Patent No.: US 7,507,712 B2
(45) Date of Patent: Mar. 24, 2009

(54) NOV PROTEIN: AN ANTI-ANGIOGENIC AGENT AND ITS USE, IN PARTICULAR FOR THE TREATMENT OF CANCER

(75) Inventors: Jean Plouët, Paris (FR); Maryvonne Laurent-Beubry, Massy (FR); Cecile Martinerie-Kryceve, Palaiseau (FR)

(73) Assignees: Centre National de la Recherche Scientifique, Paris (FR); INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 10/566,679

(22) PCT Filed: Jul. 30, 2004

(86) PCT No.: PCT/FR2004/002050

§ 371 (c)(1),
(2), (4) Date: Aug. 14, 2006

(87) PCT Pub. No.: WO2005/011725

PCT Pub. Date: Feb. 10, 2005

(65) Prior Publication Data

US 2007/0059314 A1 Mar. 15, 2007

(30) Foreign Application Priority Data

Aug. 1, 2003 (FR) .................................. 03 09506

(51) Int. Cl.
*A61K 38/16* (2006.01)
*A61K 38/17* (2006.01)
*A61K 38/18* (2006.01)
*C07K 14/435* (2006.01)
*C07K 14/475* (2006.01)

(52) U.S. Cl. .................. 514/12; 530/350; 530/399

(58) Field of Classification Search .................. None
See application file for complete search history.

(56) References Cited

U.S. PATENT DOCUMENTS 5,780,263 A * 7/1998 Hastings et al. ............ 435/69.1

FOREIGN PATENT DOCUMENTS

EP    1 382 347 A    1/2004

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Pettit et al. (1998). The development of site-specific drug-delivery systems for protein and peptide biopharmaceuticals. Trends in Biotechnology. 16: 343-349.*
International Search Report of PCT/FR2004/002050, mailed Apr. 7, 2005.
Perbal et al., "The C-terminal domain of the regulatory protein NOVH is sufficient to promote interaction with fibulin 1C: A clue for a role of NOVH in cell-adhesion signaling", Proceedings of the National Academy of Sciences of the United States of America, vol. 96, No. 3, Feb. 2, 1999, pp. 869-874, XP002322020.
Iruela-Arispe et al., "Inhibition of Angiogenesis by Thrombospondin-1 is Mediated by 2 Independent Regions Within the Type 1 Repeats", Circulation, American Heart Association, vol. 100, No. 13, Sep. 28, 1999, pp. 1423-1431, XP000923386.
Isao et al., "Connective tissue growth factor binds vascular endothelial growth factor (VEGF) and inhibits VEGF-induced angiogenesis", FASEB Journal, 'Online!, Feb. 14, 2001, pp. 1-27, XP002321942.
Isao et al., The Faseb Journal, vol. 16, No. 2, Feb. 2002, pp. 219-221.
Gupta et al., "Inhibition of Glioma Cell Growth and Tumorigenic Potential by CCN# (NOV)", Journal of Clinical Pathology: Molecular Pathology, vol. 54, No. 5, Oct. 2001, pp. 293-299, XP008010748.
Lin et al., "CCN3 (NOV) is a Novel Angiogenic Regulator of the CCN Protein Family", Journal of Biological Chemistry, vol. 278, No. 26, Jun. 27, 2003, pp. 24200-24208, XP002272895.
Lau et al., "The CCN Family of Angiogenic Regulators: the Integrin Connection", Experimental Cell Research, vol. 248, 1999, pp. 44-57, XP002272896.
Mo et al, Molecular and Cellular Biology, Dec. 2002, vol. 22, No. 24, pp. 8709-8720.
Perbal, Clin Pathol: Mol Pathol 2001; 54:57-79.
Kim et al, "Lipopolysaccharide Activates Matrix Metalloproteinase-2 in Endothelial Cells through an NF-*k*B-Dependent Pathway", Biochemical and Biophysical Research Communications 269, 401-405 (2000).
Norrby, "In vivo models of angiogenesis", J. Cell. Mol. Med., vol. 10, No. 3, 2006, pp. 588-612.

* cited by examiner

*Primary Examiner*—Christine J Saoud
*Assistant Examiner*—Jon M Lockard
(74) *Attorney, Agent, or Firm*—Nixon & Vanderhye P.C.

(57) ABSTRACT

The present invention relates to the use of a protein characterized in that it comprises or is constituted by the NOV protein, represented by the sequence SEQ ID NO: 2, or a fragment of this protein, providing that this fragment exhibits an angiogenesis-inhibiting activity, or any sequence derived from the sequence SEQ ID NO: 2 or from a fragment defined above, providing that this derived sequence exhibits an angiogenesis-inhibiting activity, or any sequence homologous to the sequence SEQ ID NO: 2 or to a fragment defined above, providing that this homologous sequence exhibits an angiogenesis-inhibiting activity, for the preparation of a medicament intended for the treatment of pathologies requiring the inhibition of endothelial proliferation or of pathologies requiring the inhibition of endothelial activation.

14 Claims, 6 Drawing Sheets

NOV (µg/ml)

FIGURE 3

NOV (µg/ml)

FIGURE 4

NOV PROTEIN: AN ANTI-ANGIOGENIC AGENT AND ITS USE, IN PARTICULAR FOR THE TREATMENT OF CANCER

This application is the US national phase of international application PCT/FR2004/002050, filed 30 Jul. 2004, which designated the U.S. and claims priority of FR 0309506, filed 1 Aug. 2003, the entire contents of each of which are hereby incorporated by reference.

A subject of the present invention is a novel anti-angiogenic agent, as well as its use, in particular within the framework of the treatment of cancer.

Angiogenesis is a growth process of new blood capillaries from pre-existing vessels. Three particular phenomena in particular form the basis of this process: proliferation, migration and differentiation (tubulogenesis) of the endothelial cells. Angiogenesis is activated by certain growth factors, known as angiogenic factors, such as VEGF (Vascular Endothelial Growth Factor) FGF-1 (Fibroblast Growth Factor 1) or FGF-2 (Fibroblast Growth Factor 2).

Normally, angiogenesis is essentially restricted to the female reproductive system and to the cicatrization of wounds. However, angiogenesis is also involved in numerous pathological cases, such as diabetic retinopathy, psoriasis, rheumatoid arthritis, age-related macular degeneration, and cancer. In fact, in the latter case it has been shown that the tumorous growth was significantly promoted by the appearance within these tumors of a neo-vascularization resulting in particular from the secretion of angiogenic factors by the tumors.

Numerous attempts at therapeutic treatments based on the use of anti-angiogenic proteins are in progress. Among these compounds, one of the most promising is endostatin (O'Reilly et al., 1997), which is currently undergoing Phase I clinical trials (Herbst et al., 2002). Endostatin is a protein of 20 kDa corresponding to a fragment of collagen XVIII. The action mechanism of endostatin remains unknown.

Certain therapeutic attempts are based on the elucidation of known action mechanisms. Thus endothelial cells in proliferation express integrin avb3 whereas quiescent endothelial cells do not express it (Brooks, 1994). This observation has made it possible to develop inhibitors of this molecule currently undergoing clinical trials.

Among all the molecular factors involved in the activation of angiogenesis, only VEGF has proved its effectiveness in practically all the experimental models for measuring angiogenesis activity (Ortega, 1999). Moreover, in spring 2003, Genentech published its finding that anti-VEGF antibodies exhibited an anti-tumor activity in patients suffering from cancer of the colon. Thus it is therefore of prime importance to research molecules which can bind to VEGF and thereby exhibit an anti-tumor activity comparable to that of the anti-VEGF antibodies.

The nov gene, first identified in avian nephroblastomas (Joliot et al., 1992; Martinerie and Perbal, 1991), has been cloned in humans (novH) (Martinerie et al., 1994), mice (novM) (Snaith et al., 1996) and Xenopus laevis (Ying and Ling, 1996). The NOV protein, encoded by the nov gene, the function of which is at present unknown, belongs to the CCN family (Bork, 1993) which comprises the following proteins: CYR61 (Lau and Nathans, 1985), CTGF (Bradham et al., 1991), ELM-1 or WISP-1 (Pennica et al., 1998; Hashimoto et al., 1998), R-COP or WISP-2 (Pennica et al., 1998; Kumar et al., 1999; Brigstock, 1999) and WISP-3 (Pennica et al., 1998). These proteins are all constituted by four distinct domains: an insulin-like growth factor binding protein (IGFBP), a Willebrand factor type C repeat domain, a thrombospondin type I repeat domain and a COOH-terminal domain. The proteins of the CCN family regulate different normal cell processes including proliferation, adhesion, apoptosis and chemotaxis. They are also involved in implantation, skeleton formation, embryo development and different diseases such as fibrosis, cicatrization and cancer (Chevalier et al., 1998).

The human NOV protein (NOVH) can be detected in normal tissues (kidneys, muscles, cartilage, cerebrum, lungs, ovaries, heart and adrenal cortex) at different levels (Joliot et al., 1992; Martinerie et al., 2001; Kocialkowski et al., 2001; Perbal et al., 1999) and its expression varies during development.

At present the functions performed by the NOV protein are not clearly established. It has recently been proposed that NOV could exhibit a proangiogenic action (Lin, 2003) by making it possible to bind to certain integrins (avb3, a6b1 and a5b1). Moreover these authors show that NOV exhibits a proangiogenic activity in the rabbit cornea model. However, it has been demonstrated that this test can lead to false positive results by releasing angiogenic factors synthesized and stored in the cornea (Plouëet, 1997).

Thus the present invention results from the demonstration of the anti-angiogenic activity of NOV due to its binding to VEGF.

The purpose of the present invention is to provide a novel anti-angiogenic agent having a novel action mechanism.

The present invention relates to the use:
of a protein characterized in that it comprises or is constituted by:
the NOV protein, represented by the sequence SEQ ID NO: 2, or
a fragment of this protein, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
any sequence derived from the sequence SEQ ID NO: 2 or from a fragment defined above, in particular by substitution, deletion or addition of one or more amino acids, providing that this derived sequence exhibits an angiogenesis-inhibiting activity, or
any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity,
of a nucleotide sequence characterized in that it comprises or is constituted by a nucleotide sequence coding:
either for the NOV protein as defined above,
or for a fragment of the NOV protein as defined above,
or for a sequence derived from the NOV protein as defined above,
or for a sequence homologous to the NOV protein as defined above,
said nucleotide sequence corresponding in particular to the nucleotide sequence SEQ ID NO: 1 coding for SEQ ID NO: 2, or to the sequence SEQ ID NO: 3 coding for SEQ ID NO: 4, or to the sequence SEQ ID NO: 5 coding for SEQ ID NO: 6, or to the sequence SEQ ID NO: 7 coding for SEQ ID NO: 8, or to the sequence SEQ ID NO: 9 coding for SEQ ID NO: 10, or to the sequence SEQ ID NO: 11 coding for SEQ ID NO: 12, of an anti-idiotypic antibody of the NOV protein, for the preparation of a medicament intended for the treatment:

of pathologies requiring the inhibition of endothelial proliferation, in particular within the framework of the following pathologies: age-related macular degeneration, diabetic retinopathy, rheumatoid arthritis, angiomas, angiosarcomas, in particular Castelman's disease and Kaposi's sarcoma, or of pathologies requiring the inhibition of endothelial activation, in particular within the framework of the following pathologies: allograft and xenograft rejection, acrocyanosis, scleroderma, or within the framework of the preparation of grafts between collection and transplantation.

The present invention relates to the use of a protein characterized in that it comprises or is constituted by:

the NOV protein, represented by the sequence SEQ ID NO: 2, or a fragment of this protein, providing that this fragment exhibits an angiogenesis-inhibiting activity, said fragment comprising in particular approximately 40 to approximately 180 amino acids, and preferably approximately 40 to approximately 80 amino acids, and being in particular represented by one of the following sequences SEQ ID NO: 4, SEQ ID NO: 6, SEQ ID NO: 8, SEQ ID NO: 10 or SEQ ID NO: 12, or any sequence derived from the sequence SEQ ID NO: 2 or from a fragment defined above, in particular by substitution, deletion or addition of one or more amino acids, providing that this derived sequence exhibits an angiogenesis-inhibiting activity, or any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, for the preparation of a medicament intended for the treatment:

of pathologies requiring the inhibition of endothelial proliferation, in particular within the framework of the following pathologies: age-related macular degeneration, diabetic retinopathy, rheumatoid arthritis, angiomas, angiosarcomas, in particular Castelman's disease and Kaposi's sarcoma, or of pathologies requiring the inhibition of endothelial activation, in particular within the framework of the following pathologies: allograft and xenograft rejection, acrocyanosis, scleroderma, or within the framework of the preparation of grafts between collection and transplantation.

The sequence SEQ ID NO: 2 corresponds to the human NOV protein encoded by the nucleotide sequence SEQ ID NO: 1.

The sequence SEQ ID NO: 4 corresponds to the IGFBP (insulin-like growth factor binding protein) fragment of the human NOV protein, said fragment being encoded by the nucleotide sequence SEQ ID NO: 3. This fragment comprises 72 amino acids and corresponds to the fragment of the NOV protein ranging from residue 33 to residue 104 of the sequence SEQ ID NO: 2.

The sequence SEQ ID NO: 6 corresponds to the VWC (von Willebrand factor type C repeat domain) fragment of the human NOV protein, said fragment being encoded by the nucleotide sequence SEQ ID NO: 5. This fragment comprises 67 amino acids and corresponds to the fragment of the NOV protein ranging from residue 108 to residue 174 of the sequence SEQ ID NO: 2.

The sequence SEQ ID NO: 8 corresponds to the TSP-1 (thrombospondin type I repeat domain) fragment of the human NOV protein, said fragment being encoded by the nucleotide sequence SEQ ID NO: 7. This fragment comprises 45 amino acids and corresponds to the fragment of the NOV protein ranging from residue 206 to residue 250 of the sequence SEQ ID NO: 2.

The sequence SEQ ID NO: 10 corresponds to the CT (COOH-terminal domain) fragment of the human NOV protein, said fragment being encoded by the nucleotide sequence SEQ ID NO: 9. This fragment comprises 75 amino acids and corresponds to the fragment of the NOV protein ranging from residue 264 to residue 338 of the sequence SEQ ID NO: 2.

The sequence SEQ ID NO: 12 corresponds to the C-terminal fragment of the human NOV protein, said fragment being encoded by the nucleotide sequence SEQ ID NO: 11. This fragment comprises 170 amino acids and corresponds to the fragment of the NOV protein ranging from residue 188 to residue 357 of the sequence SEQ ID NO: 2.

Angiogenesis-inhibiting activity is also designated anti-angiogenic activity. This activity can for example be detected in vitro by demonstrating inhibition of the multiplication, migration and differentiation of endothelial cells by the peptide sequences of the invention. Measurement of the inhibition of the multiplication of the endothelial cells can be carried out by culture of endothelial cells in the presence of the peptide sequence the activity of which is to be evaluated. Measurement of the inhibition of the migration of endothelial cells can be carried out by making a "wound" on a carpet of endothelial cells and then incubating the cells in the presence of the peptide sequence to be tested. The number of cells having migrated onto the wound is then measured. Measurement of the inhibition of the differentiation (tubulogenesis) of the endothelial cells can be carried out by measuring the length of tubules formed by endothelial cells cultured on gel in the presence of the peptide sequence to be tested.

Among the standard angiogenesis-measurement models there can be mentioned local delivery models such as:

sub-cutaneous injection of Matrigel (Becton Dickinson) impregnated with the compound of the invention (Inoki et al., 2002), or application to chicken chorio-allantoid membrane of an implant containing a compound of the invention (Celerier et al., 2002).

The compound of the invention can be injected by systemic route (intravenous, intraperitoneal, sub-cutaneous) into animals in which an experimental angiogenic disease has been created. The compound of the invention can also be injected directly into a tumor. Alternatively the NOV protein or fragments or the anti-idiotypic antibodies according to the invention (described hereafter) can be delivered by a gene therapy method by local or systemic route by any method allowing the expression of the protein or fragments or anti-idiotypic antibodies according to the invention (virus or plasmid containing the NOV sequence). Alternatively the NOV sequence or fragments or anti-idiotypic antibodies according to the invention can be inserted into a plasmid which is transfected into cancer cells (here the measurement consists of measuring the evolution of tumors developed from cancer cells transfected by a plasmid containing or not containing the NOV or fragment sequence). All these measurement procedures are in particular described in the article by Jain et al. (1997).

The term "anti-tumor activity" is used to designate an activity making it possible to inhibit tumorous growth and/or to induce the regression or even the disappearance of tumors. This activity can for example be detected in vivo by measuring the mass of tumors, the development of which has been induced by injection of tumor cells, in the presence and absence of administration of peptide sequences of the invention and/or of nucleic acids expressing the peptide sequences of the invention.

The expression "inhibition of endothelial proliferation" designates any substance capable of slowing down the proliferation of endothelial cells according to the test described hereafter (experimental part).

The expression "endothelial activation" corresponds to any pathology involving endothelial cells subjected to an increased concentration of VEGF relative to the non-pathological state.

According to an advantageous embodiment, the present invention relates to the use as defined above of a protein characterized in that it comprises or is constituted by the NOV protein, represented by the sequence SEQ ID NO: 2.

An advantageous use according to the present invention consists of the use as defined above of a protein characterized in that it comprises or is constituted by the NOV protein, represented by the sequence SEQ ID NO: 2, for the preparation of a medicament intended for the treatment of pathologies requiring the inhibition of endothelial proliferation, in particular within the framework of the following pathologies: age-related macular degeneration, diabetic retinopathy, rheumatoid arthritis, angiomas, angiosarcomas, in particular Castelman's disease and Kaposi's sarcoma.

An advantageous use according to the present invention is the use as defined above of a protein characterized in that it comprises or is constituted by the NOV protein, represented by the sequence SEQ ID NO: 2, for the preparation of a medicament intended for the treatment of pathologies requiring the inhibition of endothelial activation, in particular within the framework of the following pathologies: allograft and xenograft rejection, acrocyanosis, scleroderma, or within the framework of the preparation of grafts between collection and transplantation.

According to an advantageous embodiment, the present invention relates to the use as defined above of a protein characterized in that it comprises or is constituted by:
  a fragment of the NOV protein, represented by the sequence SEQ ID NO: 2, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
  any sequence derived from the sequence SEQ ID NO: 2 or from a fragment defined above, in particular by substitution, deletion or addition of one or more amino acids, providing that this derived sequence exhibits an angiogenesis-inhibiting activity, or
  any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity.

An advantageous use according to the present invention is the use as defined above of a protein characterized in that it comprises or is constituted by:
  a fragment of the NOV protein, represented by the sequence SEQ ID NO: 2, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
  any sequence derived from the sequence SEQ ID NO: 2 or from a fragment defined above, in particular by substitution, deletion or addition of one or more amino acids, providing that this derived sequence exhibits an angiogenesis-inhibiting activity, or
  any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity,
for the preparation of a medicament intended for the treatment of pathologies requiring the inhibition of endothelial proliferation, in particular within the framework of the following pathologies: age-related macular degeneration, diabetic retinopathy, rheumatoid arthritis, angiomas, angiosarcomas, in particular Castelman's disease and Kaposi's sarcoma.

An advantageous use according to the present invention is the use as defined above of a protein characterized in that it comprises or is constituted by:
  a fragment of the NOV protein, represented by the sequence SEQ ID NO: 2, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
  any sequence derived from the sequence SEQ ID NO: 2 or from a fragment defined above, in particular by substitution, deletion or addition of one or more amino acids, providing that this derived sequence exhibits an angiogenesis-inhibiting activity, or
  any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity,
for the preparation of a medicament intended for the treatment of pathologies requiring the inhibition of endothelial activation, in particular within the framework of the following pathologies: allograft and xenograft rejection, acrocyanosis, scleroderma, or within the framework of the preparation of grafts between collection and transplantation.

The present invention also relates to the use of a protein characterized in that it comprises or is constituted by:
  a fragment of the NOV protein, represented by the sequence SEQ ID NO: 2, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
  any sequence derived from the sequence SEQ ID NO: 2 or from a fragment defined above, in particular by substitution, deletion or addition of one or more amino acids, providing that this derived sequence exhibits an angiogenesis-inhibiting activity, or any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, for the preparation of a medicament intended for the treatment of cancer.

The present invention also relates to the use:

of a protein characterized in that it comprises or is constituted by:

the NOV protein, represented by the sequence SEQ ID NO: 2, or a fragment of this protein, providing that this fragment exhibits an angiogenesis-inhibiting activity, said fragment comprising in particular approximately 40 to approximately 80 amino acids, and being in particular represented by one of the following sequences SEQ ID NO: 4, SEQ ID NO: 6, SEQ ID NO: 8 or SEQ ID NO: 10, or any sequence derived from the sequence SEQ ID NO: 2 or from a fragment defined below, in particular by substitution, deletion or addition of one or more amino acids, providing that this derived sequence exhibits an angiogenesis-inhibiting activity, or any sequence homologous to the sequence SEQ ID NO: 2 or to a fragment defined below, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, of a nucleotide sequence characterized in that it comprises or is constituted by a nucleotide sequence coding:

either for the NOV protein as defined above, or for a fragment of the NOV protein as defined above, or for a sequence derived from the NOV protein as defined above, or for a sequence homologous to the NOV protein as defined above, said nucleotide sequence corresponding in particular to the nucleotide sequence SEQ ID NO: 1 coding for SEQ ID NO: 2, or to the sequence SEQ ID NO: 3 coding for SEQ ID NO: 4, or to the sequence SEQ ID NO: 5 coding for SEQ ID NO: 6, or to the sequence SEQ ID NO: 7 coding for SEQ ID NO: 8, or to the sequence SEQ ID NO: 9 coding for SEQ ID NO: 10, of an anti-idiotypic antibody of the NOV protein, for the preparation of a medicament intended for the treatment of pathologies requiring the inhibition of endothelial proliferation, in particular within the framework of the following pathologies: cancer, age-related macular degeneration, diabetic retinopathy, rheumatoid arthritis, angiomas, angiosarcomas, in particular Castelman's disease and Kaposi's sarcoma.

The present invention also relates to the use of a protein characterized in that it comprises or is constituted by:

the NOV protein, represented by the sequence SEQ ID NO: 2, or a fragment of this protein, providing that this fragment exhibits an angiogenesis-inhibiting activity, said fragment comprising in particular approximately 40 to approximately 80 amino acids, and being in particular represented by one of the following sequences SEQ ID NO: 4, SEQ ID NO: 6, SEQ ID NO: 8 or SEQ ID NO: 10, or any sequence derived from the sequence SEQ ID NO: 2 or from a fragment defined below, in particular by substitution, deletion or addition of one or more amino acids, providing that this derived sequence exhibits an angiogenesis-inhibiting activity, or any sequence homologous to the sequence SEQ ID NO: 2 or to a fragment defined below, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, of a nucleotide sequence characterized in that it comprises or is constituted by a nucleotide sequence coding:

either for the NOV protein as defined above, or for a fragment of the NOV protein as defined above, or for a sequence derived from the NOV protein as defined above, or for a sequence homologous to the NOV protein as defined above, said nucleotide sequence corresponding in particular to the nucleotide sequence SEQ ID NO: 1 coding for SEQ ID NO: 2, or to the sequence SEQ ID NO: 3 coding for SEQ ID NO: 4, or to the sequence SEQ ID NO: 5 coding for SEQ ID NO: 6, or to the sequence SEQ ID NO: 7 coding for SEQ ID NO: 8, or to the sequence SEQ ID NO: 9 coding for SEQ ID NO: 10, of an anti-idiotypic antibody of the NOV protein, for the preparation of a medicament intended for the treatment of pathologies requiring the inhibition of endothelial activation, in particular within the framework of the following pathologies: allograft and xenograft rejection, acrocyanosis, scleroderma, or within the framework of the preparation of grafts between collection and transplantation.

The present invention relates to a pharmaceutical composition characterized in that it contains as active ingredient:

a protein characterized in that it comprises or is constituted by:

the NOV protein, represented by the sequence SEQ ID NO: 2, or a fragment of this protein, providing that this fragment exhibits an angiogenesis-inhibiting activity, said fragment comprising in particular approximately 40 to approximately 180 amino acids, preferably approximately 40 to approximately 80 amino acids, and being in particular represented by one of the following sequences SEQ ID NO: 4, SEQ ID NO: 6, SEQ ID NO: 8, SEQ ID NO: 10 or SEQ ID NO: 12, or any sequence derived from the sequence SEQ ID NO: 2 or from a fragment defined below, in particular by substitution, deletion or addition of one or more amino acids, providing that this derived sequence exhibits an angiogenesis-inhibiting activity, or any sequence homologous to the sequence SEQ ID NO: 2 or to a fragment defined below, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, a nucleotide sequence characterized in that it comprises or is constituted by a nucleotide sequence coding:
either for the NOV protein as defined above,
or for a fragment of the NOV protein as defined above,
or for a sequence derived from the NOV protein as defined above,
or for a sequence homologous to the NOV protein as defined above, said nucleotide sequence corresponding in particular to the nucleotide sequence SEQ ID NO: 1 coding for SEQ ID NO: 2, or to the sequence SEQ ID NO: 3 coding for SEQ ID NO: 4, or to the sequence SEQ ID NO: 5 coding for SEQ ID NO: 6, or to the sequence SEQ ID NO: 7 coding for SEQ ID NO: 8, or to the sequence SEQ ID NO: 9 coding for SEQ ID NO: 10, or to the sequence SEQ ID NO: 11 coding for SEQ ID NO: 12, an anti-idiotypic antibody of the NOV protein, in combination with a pharmaceutically acceptable vector.

The present invention also relates to a pharmaceutical composition characterized in that it contains as active ingredient a protein characterized in that it comprises or is constituted by:
a fragment of the NOV protein, represented by the sequence SEQ ID NO: 2, providing that this fragment exhibits an angiogenesis-inhibiting activity, said fragment comprising in particular approximately 40 to approximately 180 amino acids, and being in particular represented by one of the following sequences SEQ ID NO: 4, SEQ ID NO: 6, SEQ ID NO: 8, SEQ ID NO: 10 or SEQ ID NO: 12, or
any sequence derived from the sequence SEQ ID NO: 2 or from a fragment defined above, in particular by substitution, deletion or addition of one or more amino acids, providing that this derived sequence exhibits an angiogenesis-inhibiting activity, or
any sequence homologous to the sequence SEQ ID NO: 2 or to a fragment defined above, preferably having a homology of at least approximately 80%, and in particular 85%, with the region comprised between the amino acids in positions (33) and (338) of the sequence SEQ ID NO: 2, providing that this homologous sequence exhibits an angiogenesis-inhibiting activity, in combination with a pharmaceutically acceptable vector.

An advantageous pharmaceutical composition according to the invention contains, as active ingredient, the abovementioned fragment TSP-1 (SEQ ID NO: 8).

An advantageous composition according to the invention is characterized in that the angiogenesis-inhibiting activity is measured according to the proliferation, migration or differentiation test, and in that this inhibition activity corresponds to an inhibition percentage comprised from 20% to 100% of the angiogenesis obtained in the presence of the vehicle alone.

The proliferation, migration or differentiation tests (angiogenesis in vitro) are described hereafter in the experimental part.

The present invention also relates to a composition as defined above, characterized in that it contains as active ingredient the NOV protein, represented by the sequence SEQ ID NO: 2.

According to an advantageous embodiment of the present invention, the composition as defined above is characterized in that it is capable of being administered at a rate of approximately 0.1 to approximately 20 mg/kg/day.

The present invention also relates to the use as defined above, for the preparation of a composition as defined above, intended to be administered at a rate of approximately 0.1 to approximately 20 mg/kg/day.

The present invention also relates to a composition as defined above characterized in that it is administered in the form of a gene, protein or peptide containing the sequence of type TSP-1 (SEQ ID NO: 8).

An advantageous composition of the invention is in particular administered preferably in injectable form.

The NOV protein (4 μg/ml) is immobilized on plastic according to the conditions described in the experimental part, then incubated with iodized $VEGF_{165}$ (1 ng/well) in the absence (PBS column) or presence of 2 μg/ml of $VEGF_{165}$ (0 column) or of NOV (NOV column). The results are expressed in cpm of fixed iodized $VEGF_{165}$ per well, after washing.

Figure 2:
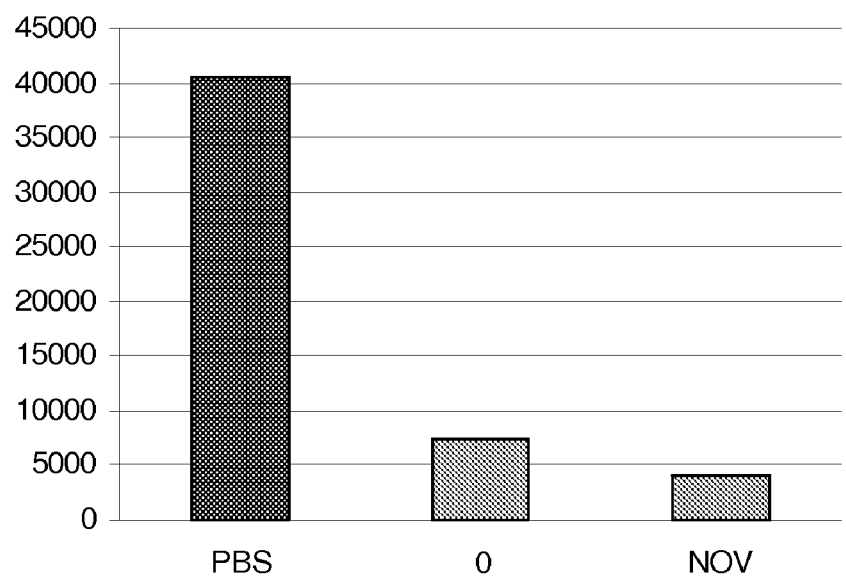

FIG. 2 corresponds to the binding of the iodized form of $VEGF_{189}$ to the NOV protein.

The NOV protein (4 μg/ml) is immobilized on plastic according to the conditions described in the experimental part, then incubated with iodized $VEGF_{189}$ (1 ng/well) in the absence (PBS column) or presence of 2 μg/ml of $VEGF_{189}$ (0 column) or NOV (NOV column). The results are expressed in cpm of fixed iodized $VEGF_{189}$ per well, after washing.

Figures 3, 4:
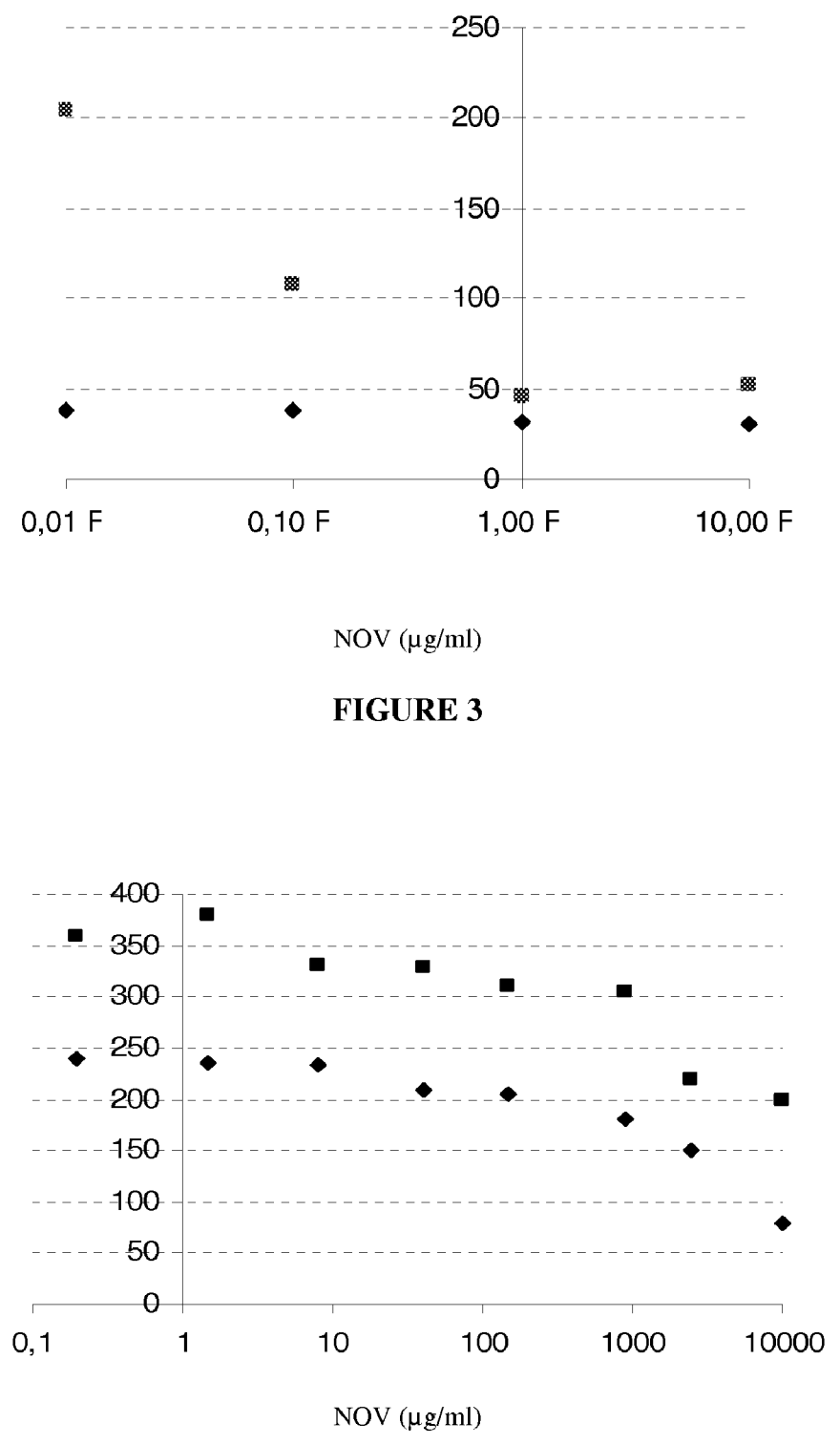

FIG. 3 corresponds to the cell migration test. The cells are counted in 8 fields and the average is represented on the y-axis. The x-axis corresponds to the concentration of the NOV protein in μg/ml. The points represented by diamonds correspond to the cells not incubated with VEGF and the points represented by squares correspond to the cells previously treated with VEGF.

FIG. 4 corresponds to the cell proliferation test. The x-axis corresponds to the concentration of the NOV protein in μg/ml and the y-axis to the optical density measured at 595 nm. The points represented by diamonds correspond to the cells which have not been stimulated by VEGF and the points represented by squares correspond to the cells which have been stimulated by VEGF.

Figure 5:
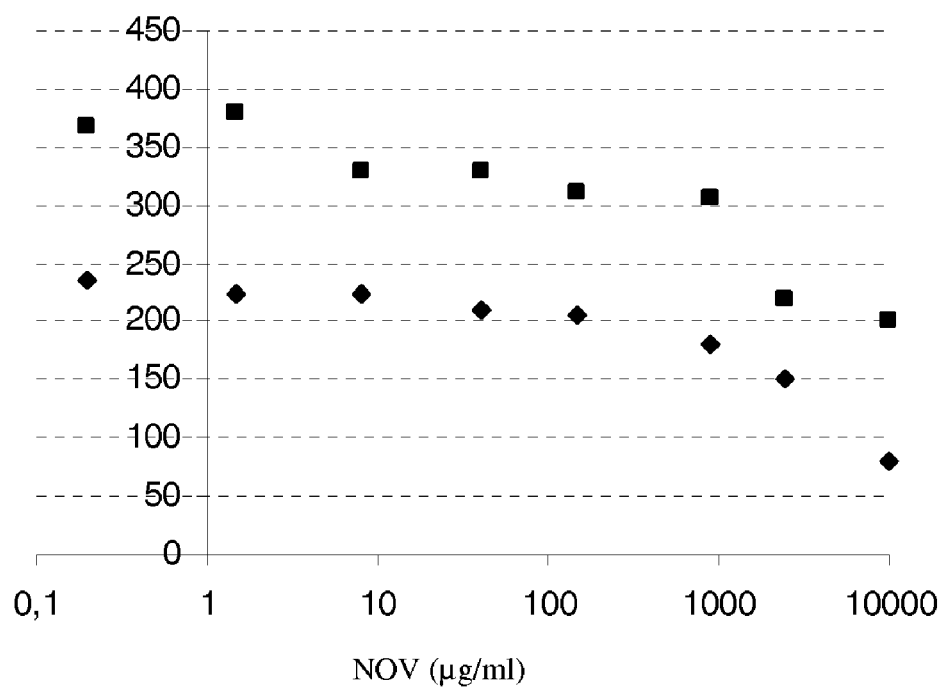

FIG. 5 corresponds to the FBAE cell adhesion test. The x-axis corresponds to the concentration of the NOV protein in μg/ml and the y-axis to the optical density measured at 595 nm. The points represented by diamonds correspond to the cells not incubated with VEGF and the points represented by squares correspond to the cells previously treated with VEGF.

Figures 6A, 6B:
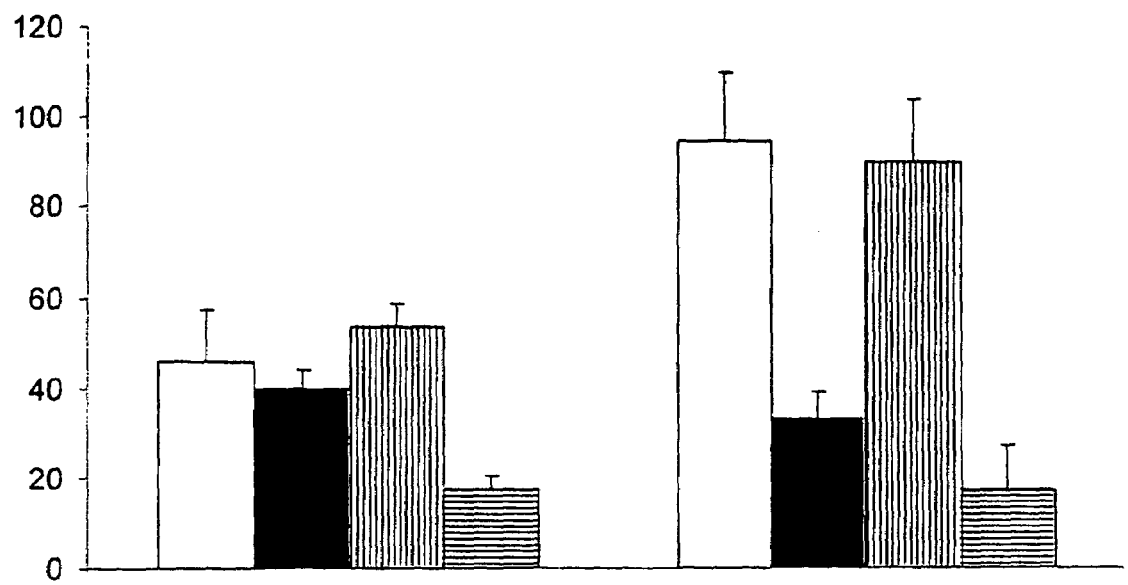

FIGS. 6A and 6B represent the effect of NOV and its fragments on the migration of HUAEC cells stimulated with $VEGF_{165}$. FIG. 6A corresponds to the control tests with cells not stimulated with $VEGF_{165}$ and FIG. 6B corresponds to the tests with cells stimulated with $VEGF_{165}$. The columns represent the number of cells/field. The white columns correspond to the control cells (without addition of NOV or one of its fragments); the black columns correspond to the cells stimulated in the presence of NOV; the vertically hatched columns correspond to the cells stimulated in the presence of the N-terminal fragment of NOV (amino acids 1 to 187 of NOV) and the horizontally hatched columns correspond to the cells stimulated in the presence of the C-terminal fragment of NOV.

Figure 7A:
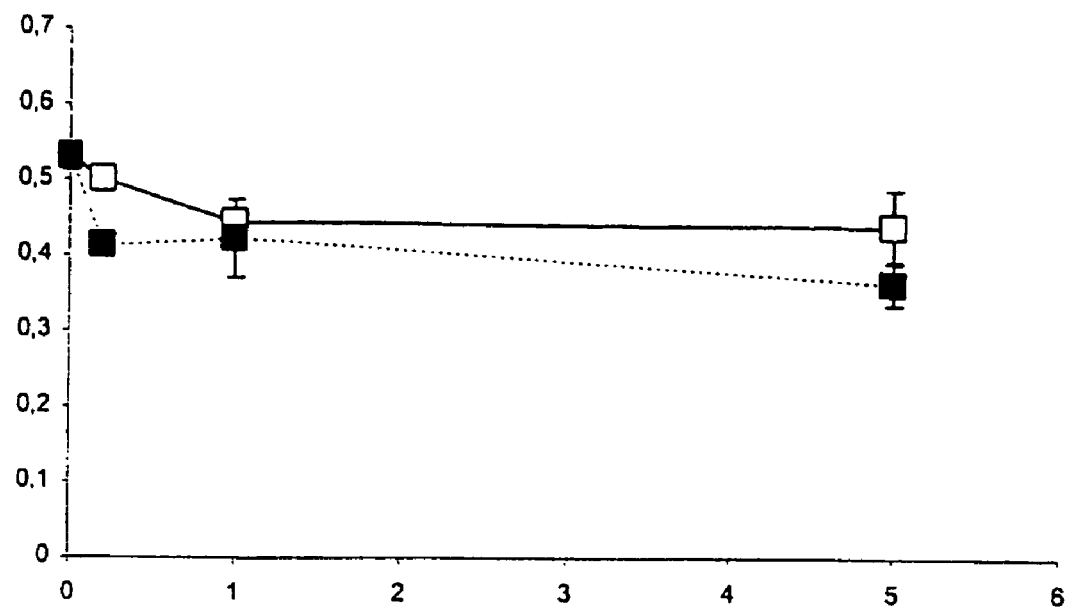

FIG. 7A represents the effect of the NOV protein or its C-terminal fragment on the proliferation of the HUAECs (human umbilical artery endothelial cells) stimulated with $VEGF_{165}$. The x-axis corresponds to the concentration of the NOV protein or the C-terminal fragment (SEQ ID NO: 12) in µg/ml and the y-axis to the optical density measured at 595 nm. The solid-line curve with the white squares corresponds to the NOV protein and the dotted-line curve with the black squares corresponds to the fragment SEQ ID NO: 12.

Figure 7B:
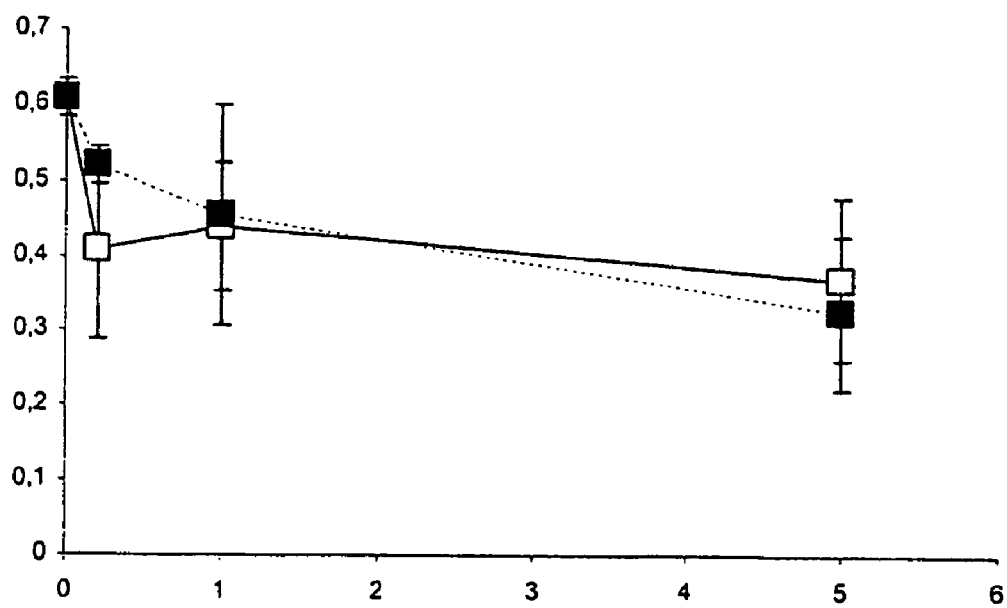

FIG. 7B represents the effect of the NOV protein or its C-terminal fragment on the proliferation of the HUAECs stimulated with bFGF. The x-axis corresponds to the concentration of the NOV protein or the C-terminal fragment (SEQ ID NO: 12) in µg/ml and the y-axis to the optical density measured at 595 nm. The solid-line curve with the white squares corresponds to the NOV protein and the dotted-line curve with the black squares corresponds to the fragment SEQ ID NO: 12.

Figure 8A:
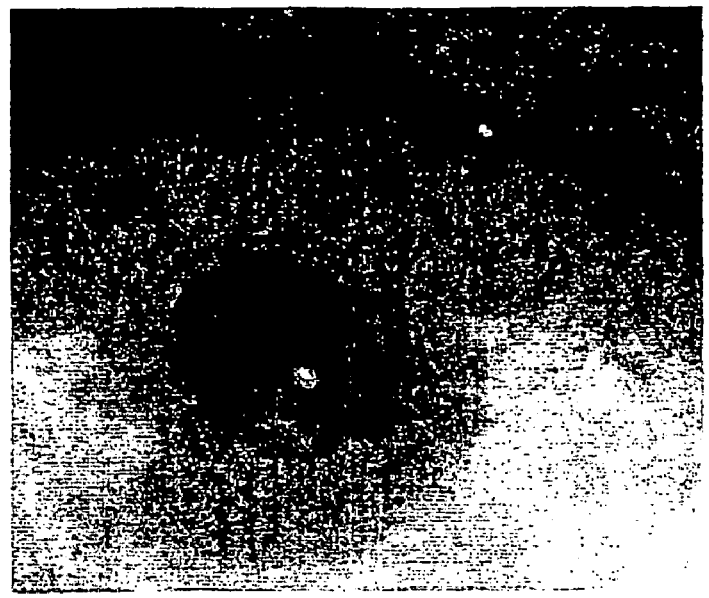
Figure 8B:
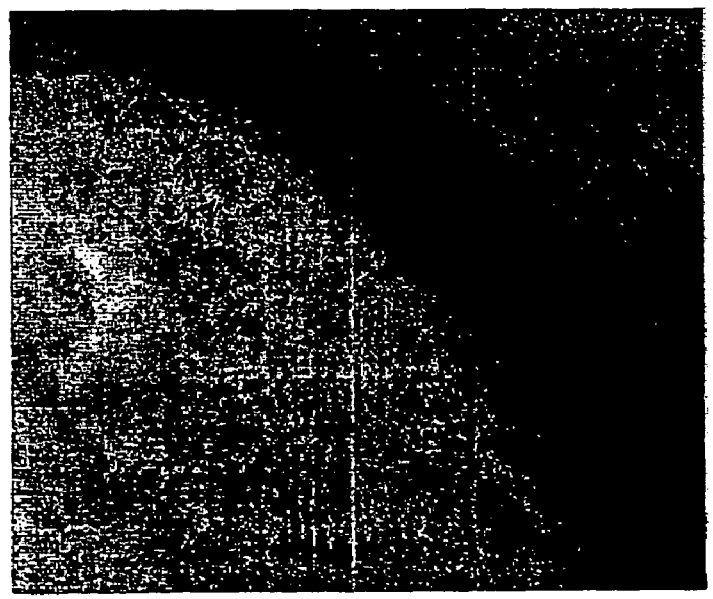

FIGS. 8A and 8B represent the effect of the C-terminal fragment of the NOV protein (SEQ ID NO: 12) on corneal angiogenesis. FIG. 8A corresponds to the injection of LPS alone and FIG. 8B to the injection of LPS and said C-terminal fragment.

EXPERIMENTAL PART

Materials:

The NOV molecule is produced by infection of SF9 insect cells by a recombinant baculovirus containing the corresponding cDNA (SEQ ID NO: 1) (Thibout et al., 2003).

The VEGF isoforms of 165 and 189 amino acids are produced by infection of SF9 insect cells by a recombinant baculovirus containing the corresponding cDNA (Plouëet al., 1997).

Human umbilical artery endothelial cells (HUAECs) were isolated from umbilical arteries perfused with collagen (Sigma) in order to digest the basal membrane. The HUAEC cells were maintained in SFM (Life Sciences) with added 20% foetal calf serum (FCS) inactivated by heat. The strain cultures received 1 ng/ml of VEGF each day.

Foetal bovine aorta endothelial (FBAE) cells were isolated from foetal aortas obtained from a local abattoir. The cells were maintained in DMEM Glutamax (Life Sciences) with 10% of new-born calf serum (NBCS) inactivated by heat, 100 µg/ml of penicillin and 100 µg/ml of streptomycin at 37° C. in 10% $CO_2$ and 1 ng/ml of VEGF added every 2 days.

Direct Interaction Between VEGF and NOV

For the binding to the immobilized NOV protein, 96-well ELISA plates were covered with 4 µg/ml of NOV protein in a 0.05 M carbonate buffer, at pH 9.6, overnight at 4° C. The non-specific binding sites were blocked with 5 mg/ml of BSA in carbonate buffer. After washing the wells twice with PBS, at pH 7.4, 1 ng of iodized VEGF was added to each well in the presence or absence of 2 µg/ml of $VEGF_{165}$ or NOV, diluted in PBS containing 0.05% Tween 20, 0.5% BSA, 1 mM of $MgCl_2$ and 1 mM of $CaCl_2$.

The wells were washed 3 times with a mixture of PBS-Tween 20 0.1%-BSA 0.5% and the bound proteins were solubilized in 0.2M NaOH.

Figure 1:
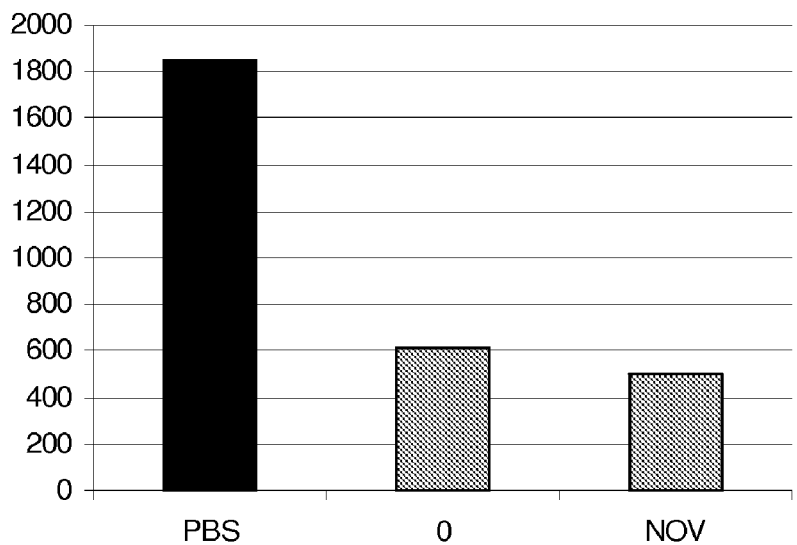
FIG. 1 corresponds to the binding of the iodized form of $VEGF_{165}$ to the NOV protein.

The results of these experiments are represented in FIGS. 1 and 2.

FIG. 1 shows that the iodized $VEGF_{165}$ specifically combines with NOV since the addition of non-radiolabelled VEGF (VEGF) inhibits this binding. Similarly, the addition of NOV inhibits the binding of radiolabelled $VEGF_{165}$ to NOV.

Migration Tests

FBAE cells are inoculated in 4 $cm^2$ wells at a high density (50,000 cells/well). When the monolayer is confluent, the proliferation is stopped by incubation, overnight, in the presence of DMEM without serum. A wound is then made in the monolayer using a foam scraper, making it possible to delimit a surface free of any cell. The monolayers are then washed 3 times with DMEM in order to remove the non-adherent cells. A photograph is then taken in order to delimit the surface before any cell migration. The wells are then incubated in DMEM alone or in the presence of 50 ng/ml of VEGF in the presence of variable concentrations of NOV. After 24 hours the wells are washed 3 times and stained with May-Grunwald-Giemsa and photographed. The photographs taken before and after the experiment are then superimposed in order to allow counting of the cells having migrated.

The results of these tests are indicated in FIG. 3.

The addition of NOV in the absence of VEGF has no effect on the basal migration of the cells. On the other hand, NOV inhibits the activity of VEGF and 50% of the maximum effect is obtained with a concentration of 50-100 ng/ml of NOV.

Proliferation Tests 96-well culture plates were seeded with 1000 FBAE cells per well in DMEM with 5% NBCS added. The cells were or were not stimulated with 2 ng/ml of $VEGF_{165}$ and different concentrations of NOV. After 5 days, the wells were gently rinsed with DMEM and the cells were fixed in 1% glutaldehyde for 20 minutes at ambient temperature. The fixed cells were quantified by incorporation of crystal violet (Kueng et al., 1989): the cells were incubated in 0.1% crystal violet (Sigma) diluted in 0.2 M of borate buffer, at pH 9.5, for 20 minutes at ambient temperature, the non-incorporated stain was eliminated by completely washing the wells with large quantities of water and the crystal violet stain incorporated was then solubilized by 100 µl of 10% acetic acid per well. The optical density readings were carried out at 595 nm. Similar results were obtained in three separate experiments (see FIG. 4). The values indicated are average optical densities of 6 wells±SD.

The NOV protein used alone has no significant effect on the basal proliferation (due to the serum alone). On the other hand, the NOV protein inhibits the proliferation induced by the VEGF in a dose-dependent manner. 50% of the maximum effect is obtained with a concentration of 100-200 ng/ml of NOV.

Cell Adhesion Tests 96-well ELISA plates (Nunc) were covered with $VEGF_{165}$ protein according to the protocol described in the article by Hutchings et al. (2003), diluted in 0.05 M carbonate buffer, at pH 9.6, overnight at 4° C. The non-specific binding sites were blocked for 1 hour at 37° C. with 5 mg/ml of BSA in carbonate buffer and washed twice with DMEM before the experiments. The cells were trypsinized, washed and re-suspended in 5 ml of DMEM with 10% FCS in an untreated plastic tube and incubated for 1 hour at 37° C. with 10% $CO_2$. The cells were then concentrated by centrifugation and re-suspended in a DMEM+0.2% BSA mixture without serum and the cell suspension was treated for 20 minutes (37° C., 10% $CO_2$) with the NOV protein used in order to modulate the adhesion. 40,000 cells per well were distributed in the wells in a volume of 100 µl of DMEM+0.2% BSA. The cells were left to adhere at 37° C. under 10% $CO_2$ for the desired time. The wells were gently washed three times with DMEM in order to remove the non-adherent cells and the adherent cells were fixed with 1% glutaraldehyde for 20 minutes at ambient temperature. The fixed cells were quantified by incorporation of crystal violet (Kueng et al., 1989): the cells were incubated with 0.1% crystal violet (Sigma) diluted in 0.2 M of borate buffer, at pH 9.5, for 20 minutes at ambient temperature, the non-incorporated stain was eliminated by completely washing the wells with large quantities of water and the crystal violet stain incorporated was then solubilized by 100 μl of 10% acetic acid per well (see FIG. 5).

In Vitro Angiogenesis

Four rats' tails were skinned and dissected in order to recover the white fasciculi which are mostly constituted by type I collagen. The collagen is extracted from these fibres in 50 ml of cold 0.5 M acetic acid and stirred overnight. The liquid is then centrifuged at 5000 g for 40 minutes and the supernatant is recovered. The extraction is repeated once with 20 ml of acetic acid, the supernatants are mixed and then dialyzed against 1 l of 0.2 M acetic acid. The collagen concentration is adjusted to 3 mg/ml by weight. The preparation of gels for the in vitro angiogenesis is carried out on ice in order to preserve the collagen solution in liquid form. One ml of collagen (5 mg/ml) is mixed with 0.5 ml of 10× DMEM (containing a 10× concentration of antibiotics and glutamine), 0.9 ml of sterile $H_2O$ and 0.1 ml of 1M sodium bicarbonate. Once the pH has been adjusted to 7.4, an equal volume of matrigel (Becton Dickinson) is added. The gel is poured into culture wells (2 mm thick) and incubated at 37° C. in order to solidify. The cells are added after 15 minutes (100,000 cells/cm$^2$) onto the surface of the gel. After 2 hours, the different soluble factors are added and the cells are observed and photographed after 24 hours.

Production of Anti-idiotypic Antibodies

Firstly, an NOV-neutralizing antibody is prepared by injecting an animal, in particular a mouse, with NOV protein mixed with Freund's complete adjuvant (1 volume per volume of NOV protein). A quantity of NOV comprised between 1 and 200 μg/kg of body weight is chosen in order to immunize the animal. The same operation is carried out at intervals of 15 and 30 days, except that the complete adjuvant is replaced by incomplete adjuvant. On day 40 bleeding is carried out, the serum is separated and the immunoglobulins are purified by any usual method of fractionation, in particular precipitation with ammonium sulphate, protein A or G affinity chromatography. The immunoglobulin-neutralizing activity is measured by any test described (binding of the iodized VEGF, cell proliferation, migration, adhesion). A batch of immunoglobulins is referred to as neutralizing when it has the ability to inhibit the interaction of NOV with VEGF.

Secondly, anti-idiotypic antibodies of NOV are prepared by injecting mice by sub-cutaneous route with 1-100 μg of the preparation of the immunoglobulins neutralizing the NOV activity described previously in combination with 100 μl of adjuvant, in particular Freund's complete adjuvant (Sigma). The injection is repeated 15, 30 and 45 days later. Fifty-five days after the first injection, mice are injected with 10 μg of the same antibody by intraperitoneal route. Fifty-eight days after the first injection, the mice are sacrificed and their spleens are removed and dilacerated in ISCOVE's medium in order to release the splenocytes. The splenocytes are fused with mouse myeloma cells, in particular AG8X 63 cells (Kearney et al., 1979), and incubated at a rate of 100,000 cells/well. The fusion is carried out by the addition of 20 times 50 μl of polyethylene glycol (PEG) at 30-second intervals. Four ml of ISCOVE's medium preheated at 37° C. is then added dropwise to the cell suspension, then after a period of incubation of 4 minutes at 37° C., 4 ml is added. The suspension is centrifuged then the cell pellet is taken up in 100 ml of ISCOVE's medium complemented with 20% foetal calf serum and 1×HAT (50×: 5 mM Hypoxanthine, 20 μM Aminopterin and 0.8 mM Thymidine) and distributed at a rate of 100 μl per well on the macrophages. After 5 days, 100 μl of HAT medium is added, and between 8 and 14 days the conditioned medium of each hybridoma is removed in order to measure by ELISA the antibodies directed against the antibodies having served as immunogenic agent, i.e. the anti-NOV antibodies. The activity of the anti-idiotypic antibodies is then measured by an ELISA test:

The Fab fragments of the anti-NOV immunoglobulins, prepared by any standard technique, in particular papain digestion, are immobilized on microtitration plates (0.1-20 μg/ml in 50 mM carbonate buffer, pH 9.6). After saturation of the non-specific sites by a solution of albumin serum diluted to 5 mg/ml in the same buffer, the hybridoma culture supernatants are added diluted by half in PBS buffer containing 0.05% Tween 20. After rinsing, the anti-idiotypic antibodies are developed by the addition of an appropriate concentration of anti-Fc antibodies of mice coupled with peroxidase. The quantity of fixed anti-idiotypic antibodies is then measured by development of the peroxidase and is proportional to the intensity of the calorimetric reaction.

The hybridomas selected by their capacity to secrete antibodies directed against anti-NOV antibodies are then cloned, i.e. the cells are seeded under limited dilution conditions (5 cells/ml) under a volume of 0.1 ml per well. The medium is changed after 10 days. After 15 days, certain wells contain foci of cells which are multiplied from the cell seeded at the start, therefore all these cells are identical and originate from the same clone. When the surface occupied by the cells represents at least half of the total surface of the well, the medium is removed and analyzed as previously by an ELISA test on anti-NOV Fab. At this stage the antibody-producing clones can be selected and their specificity known.

Once the clones are identified, their monoclonal nature is affirmed by the standard operation consisting of seeding a 96-well plate with cells originating from the same clone diluted under limiting conditions as previously. The secreting clones must therefore all secrete an antibody of the same specificity in order for this antibody to be declared monoclonal. A third cloning is then carried out under exactly the same conditions in order to ensure that the clones are indeed monoclonal.

The anti-idiotypic antibodies are screened by a battery of tests, in particular by an ELISA test on immobilized VEGF. VEGF is immobilized (0.1-10 μg/ml) in carbonate buffer as previously and all the stages of this ELISA test are identical to those described in the ELISA test on anti-NOV Fab. This test makes it possible to screen from all the anti-idiotypic antibodies those which mimic the functions of the NOV protein (SEQ ID NO: 2) or type TSP-1 fragments (SEQ ID NO: 8), i.e. antibodies recognizing VEGF.

CONSTRUCTION OF NOV MUTANTS

Deletion mutants of the NOV protein were constructed according to the reference (Perbal et al., 1999) and produced in a baculovirus expression system:

N-Ter (corresponds to a sequence comprising the amino acids 1-187 of NOV) and

C-Ter containing the amino acids 188 to 357 (this sequence contains the thrombospondin type domain (SEQ ID NO: 8) and the C-terminal domain rich in cysteines (SEQ ID NO: 10).

Migration Tests (FIG. 6)

HUAEC cells are inoculated in 4 cm$^2$ wells at a high density (50,000 cells/well). When the monolayer is confluent, proliferation is stopped by incubation, overnight, in the presence of SFM with 1% NBCS. A wound is then made in the monolayer using a foam scraper, making it possible to delimit a surface free of any cell. The monolayers are then washed 3 times with SFM in order to remove the non-adherent cells. A photograph is then taken in order to delimit the surface before any cell migration. The wells are then incubated in SFM alone or in the presence of 50 ng/ml of VEGF in the presence of variable concentrations of NOV or of its N-Ter or C-Ter fragments. After 24 hours the wells are washed 3 times and stained with May-Grunwald-Giemsa and photographed. The photographs taken before and after the experiment are then superimposed in order to allow counting of the cells having migrated.

The results of these tests are indicated in FIG. 6.

The addition of NOV or the N-Ter fragment in the absence of VEGF has no effect on the basal migration of the cells. NOV inhibits the activity of VEGF and 50% of the maximum effect is obtained with a concentration of 50-100 ng/ml of NOV. The N-Ter fragment exhibits no inhibiting activity. On the other hand, the C-Ter fragment inhibits the migration of the HUAEC cells.

These experiments demonstrate that the NOV sequence comprising the amino acids 188 to 357 is indeed responsible for angiogenesis-inhibiting activity due to VEGF and that it induces an activity inhibiting migration, including in the absence of VEGF.

Proliferation Tests (FIG. 7)

96-well culture plates were seeded with 2000 HUAEC cells per well in SFM medium with 10% NBCS added. The cells were or were not stimulated with 2 ng/ml of $VEGF_{165}$ and different concentrations of NOV or C-Ter fragment. After 5 days, the wells were gently rinsed with SFM medium and the cells were fixed in 1% glutaldehyde for 20 minutes at ambient temperature. The fixed cells were quantified by incorporation of crystal violet: the cells were incubated in 0.1% crystal violet (Sigma) diluted in 0.2 M of borate buffer, at pH 9.5, for 20 minutes at ambient temperature, the non-incorporated stain was eliminated by completely washing the wells with large quantities of water and the crystal violet stain incorporated was then solubilized by 100 µl of 10% acetic acid per well. The optical density readings were carried out at 595 nm. Similar results were obtained in three separate experiments (see FIG. 7). The values indicated are average optical densities of 6 wells±SD.

The NOV protein inhibits the proliferation induced by VEGF and FGF in a dose-dependent manner. 50% of the maximum effect is obtained with an inhibiting concentration of 50% of 200 ng/ml of NOV vis-à-vis VEGF and FGF. Similarly, the C-Ter fragment inhibits the proliferation induced by VEGF and FGF with a concentration of 200 ng/ml.

These experiments demonstrate that the NOV sequence comprising the amino acids 188 to 357 is indeed responsible for angiogenesis-inhibiting activity. The observation according to which the mitogenic activity of the FGF is also inhibited by the NOV fragment 188-357 demonstrates that the inhibiting activity is not restricted to the single factor VEGF.

Corneal Angiogenesis

Wistar rats are anaesthetized. The corneas are incised and a corneal pocket is obtained by dilacerating the thickness of the stroma using a foam spatula. An Elvax implant (DuPont) containing lipopolysaccharide, an inflammatory agent triggering an angiogenic reaction dependent on several angiogenic factors, is inserted into the bottom of the pocket. After 8 days an angiogenic reaction is visible with respect to the limbus. When the C-Ter fragment is injected into the corneal pocket (5 µg every 2 days between D4 and D8), the angiogenic reaction is completely inhibited (FIG. 8).

These experiments demonstrate that the C-Ter fragment of NOV exhibits a major anti-angiogenic activity, being dependent on the activation of several angiogenic factors.

REFERENCES

Bork P (1993) The modular architecture of a new family of growth regulators related to connective tissue growth factor. *FEBS Lett.* 327: 125-130, Bradham D M, Igarashi A, Potter R L, Grotendorst G R (1991) Connective tissue growth factor: a cysteine-rich mitogen secreted by human vascular endothelial cells is related to the SRC-induced immediate early gene product CEF-10. *J Cell Biol.* 114:1285-1294, Brigstock D R (1999) The connective tissue growth factor/cysteine-rich 61/nephroblastoma overexpressed (CCN) family. *Endocrine Rev.* 20:189-206, Brooks P C, Clark R A, Cheresh D A (1994) Requirement of vascular integrin alpha v beta 3 for angiogenesis. *Science,* 264, 569-71, Celerier J, Cruz A, Lamande N, Gasc J M, Corvol P (2002) Angiotensinogen and its cleaved derivatives inhibit angiogenesis. *Hypertension.* 39(2):224-8, Chevalier G, Yeger H, Martinerie C, et al. (1998) nov H: Differential expression in developing kidney and in Wilms' tumors. *Am J Pathol.* 152:1563-1575, Hashimoto Y, Shindo-Okada N, Tani M, et al. (1998) Expression of the Elm-1 gene, a novel gene of the CCN (CTGF, Cyr61/Cef10 and nov) family, suppress in vivo growth and metastasis of K-1735 murine melanoma cells. *J Exp Med.* 187:289-296, Herbst et al. (2002) *J. Clin. Oncol.* 20:3804-3814, Hutchings H, Ortéga N, Plouët J (2003) Extracellular matrix bound vascular endothelial growth factor promotes endothelial cell adhesion, migration and survival through integrin ligation. *FASEB J.* April 22 (Epub ahead of print)

Inoki I, Shiomi T, Hashimoto G, Enomoto H, Nakamura H, Makino K, Ikeda E, Takata S, Kobayashi K, Okada Y (2002) Connective tissue growth factor binds vascular endothelial growth factor (VEGF) and inhibits VEGF-induced angiogenesis. *FASEB J.* 16(2):219-21, Jain R K, Schlenger K, Hockel M, Yuan F (1997) Quantitative angiogenesis assays: progress and problems. Nat Med. 3(11):1203-8, Joliot V, Martinerie C, Dambrine G, et al. (1992) Proviral rearrangements and overexpression of a new cellular gene (nov) in myeloblastosis-associated virus type 1-induced nephroblastomas. *Mol Cell Biol.* 12:10-21, Kearney J F, Radbruch A, Liesegang B, Rajewsky K (1979) A new mouse myeloma cell line that has lost immunoglobulin expression but permits the construction of antibody-secreting hybrid cell lines. *J. Immunol.* 123, 1548-50, Kocialkowski S Y, H. Kingdom, J. Perbal, B. Schofield, P N (2001) Expression of the human NOV gene in first trimester fetal tissues. *Anat Embryol.* 203:417-427, Kumar S, Hand A T, Connor J R, et al. (1999) Identification and cloning of a Connective tissue growth factor-like cDNA from human osteoblasts encoding a novel regulator of osteoblast functions. *J Biol Chem.* 274:17123-17131, Lau L, Nathans D (1985) Expression of a set of growth-regulated immediate early genes in BALB/c 3T3 cells: coordinate regulation with c-fos or c-myc. *Proc Natl Acad Sci USA.* 84: 1182-1186, Lin C J, Leu S-J, Chen N, Tebeau C M, Lin S-X, Yeung C-H, Lau L J, (2003) CCN3 (NOV) is a novel angiogenic regulator of the CCN protein family. *J. Biol. Chem.,* 278, 24200-24208, Martinerie C, Gicquel C, Louvel A, Laurent M, Schofield P, LeBouc Y (2001) Altered expression of NovH is associated with human adrenocortical tumorigenesis. *JCEM*. 86:3929-3940, Martinerie C, Huff V, Joubert I, et al. (1994) Structural analysis of the human nov proto-oncogene and expression in Wilms tumor. *Oncogene* 9: 2729-2732, Martinerie C, Perbal B (1991) Expression of a gene encoding a novel IGF binding protein in human tissues. *C R Acad Sci Paris*. 313: 345-351, O'Reilly et al. (1997) *Cell* 88:277-285, Ortéga N, Hutchings H, Plouët J (1999) Signal relays in the VEGF system. *Front. Biosc.*, 4, D141-D152, Pennica D, Swanson T A, Welsh J W, et al. (1998) WISP genes are members of the connective tissue growth factor family that are up-regulated in human colon tumors. *Proc Natl Acad Sci*. 95:14717-14722, Perbal B, Martinerie C, Sainson R, Werner M, He B, Roizman B (1999) The C-terminal domain of the regulatory protein NOVH is sufficient to promote interaction with fibulin 1C: a clue for a role of NOVH in cell-adhesion signaling. *Proc Natl Acad Sci U S A*. 96: 869-874, Plouët J, Moro F, Coldeboeuf N, Bertagnolli S, Clamens S, Bayard F (1997) Extracellular cleavage of the vascular endothelial growth factor 189 aa form by urokinae is required for its mitogenic activity. *J. Biol. Chem.*, 272, 13390-13396, Snaith M, Natarajan D, Taylor L, et al. (1996) Genomic structure and chromosomal mapping of the mouse nov gene. *Genomics*. 38: 425-428, Thibout H, Martinerie C, Creminon C, Godeau F, Boudou P, Le Bouc Y, Laurent M (2003) Characterization of NOVH in biological fluids: an enzyme immuno assay for the quantification of NOVH in sera from patients with diseases of the adrenal gland and of the nervous system. *J Clin Endocrinol Metab.* 88(1):327-336, Ying Z, Ling M L (1996) Isolation and characterization of xnov, a Xenopus laevis ortholog of the chicken nov gene. *Gene*. 17 1:243-248.

---

The invention claimed is:

1. A method for inhibiting endothelial proliferation or endothelial activation in a person in need thereof, said method comprising administering a pharmaceutically acceptable amount of a protein comprising the NOV protein fragment set forth in SEQ ID NO: 12 to said person.

2. The method according to claim 1, wherein said person has age-related macular degeneration, diabetic retinopathy, rheumatoid arthritis, angiomas or angiosarcomas.

3. The method according to claim 1 wherein said person has Castelman's disease or Kaposi's sarcoma.

4. The method according to claim 1, wherein said person has an allograft rejection, a xenograft rejection, acrocyanosis or scleroderma.

5. The method according to claim 1, wherein said protein consists of the NOV protein fragment set forth in SEQ ID NO: 12.

6. A method for the treatment of cancer comprising administering a pharmaceutically acceptable amount of a protein comprising the NOV protein fragment set forth in SEQ ID NO: 12 to a person in need of said treatment.

7. The method according to claim 6, wherein said protein consists of the NOV protein fragment set forth in SEQ ID NO: 12.

8. The method of claim 1 wherein said pharmaceutical composition is administered at a rate of approximately 0.1 to approximately 20 mg/kg/day.

9. The method of claim 2 wherein said pharmaceutical composition is administered at a rate of approximately 0.1 to approximately 20 mg/kg/day.

10. The method of claim 3 wherein said pharmaceutical composition is administered at a rate of approximately 0.1 to approximately 20 mg/kg/day.

11. The method of claim 4 wherein said pharmaceutical composition is administered at a rate of approximately 0.1 to approximately 20 mg/kg/day.

12. The method of claim 5 wherein said pharmaceutical composition is administered at a rate of approximately 0.1 to approximately 20 mg/kg/day.

13. The method of claim 6 wherein said pharmaceutical composition is administered at a rate of approximately 0.1 to approximately 20 mg/kg/day.

14. The method of claim 7 wherein said pharmaceutical composition is administered at a rate of approximately 0.1 to approximately 20 mg/kg/day.

* * * * *

SEQUENCE LISTING

<160> NUMBER OF SEQ ID NOS: 12

<210> SEQ ID NO 1
<211> LENGTH: 2389
<212> TYPE: DNA
<213> ORGANISM: homo sapiens
<220> FEATURE:
<221> NAME/KEY: CDS
<222> LOCATION: (73)..(1143)

<400> SEQUENCE: 1

```
gggaaggcga gcagtgccaa tctacagcga agaaagtctc gtttggtaaa agcgagaggg          60
gaaagcctga gc atg cag agt gtg cag agc acg agc ttt tgt ctc cga aag         111
              Met Gln Ser Val Gln Ser Thr Ser Phe Cys Leu Arg Lys
                1               5                   10 cag tgc ctt tgc ctg acc ttc ctg ctt ctc cat ctc ctg gga cag gtc           159
Gln Cys Leu Cys Leu Thr Phe Leu Leu Leu His Leu Leu Gly Gln Val
 15                  20                  25 gct gcg act cag cgc tgc cct ccc cag tgc ccg ggc cgg tgc cct gcg           207
Ala Ala Thr Gln Arg Cys Pro Pro Gln Cys Pro Gly Arg Cys Pro Ala
 30              35                  40                  45 acg ccg ccg acc tgc gcc ccc ggg gtg cgc gcg gtg ctg gac ggc tgc           255
Thr Pro Pro Thr Cys Ala Pro Gly Val Arg Ala Val Leu Asp Gly Cys
                 50                  55                  60 tca tgc tgt ctg gtg tgt gcc cgc cag cgt ggc gag agc tgc tca gat           303
Ser Cys Cys Leu Val Cys Ala Arg Gln Arg Gly Glu Ser Cys Ser Asp
             65                  70                  75 ctg gag cca tgc gac gag agc agt ggc ctc tac tgt gat cgc agc gcg           351
Leu Glu Pro Cys Asp Glu Ser Ser Gly Leu Tyr Cys Asp Arg Ser Ala
         80                  85                  90 gac ccc agc aac cag act ggc atc tgc acg gcg gta gag gga gat aac           399
Asp Pro Ser Asn Gln Thr Gly Ile Cys Thr Ala Val Glu Gly Asp Asn
     95                 100                 105 tgt gtg ttc gat ggg gtc atc tac cgc agt gga gag aaa ttt cag cca           447
Cys Val Phe Asp Gly Val Ile Tyr Arg Ser Gly Glu Lys Phe Gln Pro
110                 115                 120                 125 agc tgc aaa ttc cag tgc acc tgc aga gat ggg cag att ggc tgt gtg           495
Ser Cys Lys Phe Gln Cys Thr Cys Arg Asp Gly Gln Ile Gly Cys Val
                130                 135                 140
```

| | | |
|---|---|---|
| ccc cgc tgt cag ctg gat gtg cta ctg cct gag cct aac tgc cca gct<br>Pro Arg Cys Gln Leu Asp Val Leu Leu Pro Glu Pro Asn Cys Pro Ala<br>              145                        150                        155 | | 543 |
| cca aga aaa gtt gag gtg cct gga gag tgc tgt gaa aag tgg atc tgt<br>Pro Arg Lys Val Glu Val Pro Gly Glu Cys Cys Glu Lys Trp Ile Cys<br>              160                        165                        170 | | 591 |
| ggc cca gat gag gag gat tca ctg gga ggc ctt acc ctt gca gct tac<br>Gly Pro Asp Glu Glu Asp Ser Leu Gly Gly Leu Thr Leu Ala Ala Tyr<br>        175                        180                        185 | | 639 |
| agg cca gaa gcc acc cta gga gta gaa gtc tct gac tca agt gtc aac<br>Arg Pro Glu Ala Thr Leu Gly Val Glu Val Ser Asp Ser Ser Val Asn<br>190                        195                        200                        205 | | 687 |
| tgc att gaa cag acc aca gag tgg aca gca tgc tcc aag agc tgt ggt<br>Cys Ile Glu Gln Thr Thr Glu Trp Thr Ala Cys Ser Lys Ser Cys Gly<br>              210                        215                        220 | | 735 |
| atg ggg ttc tcc acc cgg gtc acc aat agg aac cgt caa tgt gag atg<br>Met Gly Phe Ser Thr Arg Val Thr Asn Arg Asn Arg Gln Cys Glu Met<br>        225                        230                        235 | | 783 |
| ctg aaa cag act cgg ctc tgc atg gtg cgg ccc tgt gaa caa gag cca<br>Leu Lys Gln Thr Arg Leu Cys Met Val Arg Pro Cys Glu Gln Glu Pro<br>              240                        245                        250 | | 831 |
| gag cag cca aca gat aag aaa gga aaa aag tgt ctc cgc acc aag aag<br>Glu Gln Pro Thr Asp Lys Lys Gly Lys Lys Cys Leu Arg Thr Lys Lys<br>        255                        260                        265 | | 879 |
| tca ctc aaa gcc atc cac ctg cag ttc aag aac tgc acc agc ctg cac<br>Ser Leu Lys Ala Ile His Leu Gln Phe Lys Asn Cys Thr Ser Leu His<br>270                        275                        280                        285 | | 927 |
| acc tac aag ccc agg ttc tgt ggg gtc tgc agt gat ggc cgc tgc tgc<br>Thr Tyr Lys Pro Arg Phe Cys Gly Val Cys Ser Asp Gly Arg Cys Cys<br>                    290                        295                        300 | | 975 |
| act ccc cac aat acc aaa acc atc cag gca gag ttt cag tgc tcc cca<br>Thr Pro His Asn Thr Lys Thr Ile Gln Ala Glu Phe Gln Cys Ser Pro<br>                    305                        310                        315 | | 1023 |
| ggg caa ata gtc aag aag cca gtg atg gtc att ggg acc tgc acc tgt<br>Gly Gln Ile Val Lys Lys Pro Val Met Val Ile Gly Thr Cys Thr Cys<br>        320                        325                        330 | | 1071 |
| cac acc aac tgt cct aag aac aat gag gcc ttc ctc cag gag ctg gag<br>His Thr Asn Cys Pro Lys Asn Asn Glu Ala Phe Leu Gln Glu Leu Glu<br>              335                        340                        345 | | 1119 |
| ctg aag act acc aga ggg aaa atg taacctatca ctcaagaagc acacctacag<br>Leu Lys Thr Thr Arg Gly Lys Met<br>350                        355 | | 1173 |
| agcacctgta gctgctgcgc cacccaccat caaaggaata taagaaaagt aatgaagaat | | 1233 |
| cacgatttca tccttgaatc ctatgtattt tcctaatgtg atcatatgag gacctttcat | | 1293 |
| atctgtcttt tatttaacaa aaaatgtaat taactgtaaa cttggaatca aggtaagctc | | 1353 |
| aggatatggc ttaggaatga cttactttcc tgtggtttta ttacaaatgc aaatttctat | | 1413 |
| aaatttaaga aaacaagtat ataatttact ttgtagactg tttcacattg cactcatcat | | 1473 |
| attttgttgt gcactagtgc aattccaaga aaatatcact gtaatgagtc agtgaagtct | | 1533 |
| agaatcatac ttaacatttc attgtacaag tattacaacc atatattgag gttcattggg | | 1593 |
| aagattctct attggctccc tttttgggta accagctct gaacttccaa gctccaaatc | | 1653 |
| caaggaaaca tgcagctctt caacatgaca tccagagatg actattactt ttctgtttag | | 1713 |
| ttttacacta ggaaacgtgt tgtatctaca gtaatgaaat gtttactaag tggactggtg | | 1773 |
| tcataaaactt tctccattta agacacattg actcctttcc aatagaaaga aactaaacag | | 1833 |
| aaaactccca atacaaagat gactggtccc tcatagccct cagacattta tatattggaa | | 1893 |

```
gctgctgagg ccccccaagtt ttttaattaa gcagaaacag catattagca gggattctct   1953
catctaactg atgagtaaac tgaggcccaa agcacttgct tacatcctct gatagctgtt   2013
tcaaatgtgc attttgtgga attttgagaa aaatagagca aaatcaacat gactggtggt   2073
gagagaccac acattttatg agagtttgga attattgtag acatgcccaa aacttatcct   2133
tgggccataa ttatgaaaac tcatgatcaa gatatatgtg tatacataca tgtatctggt   2193
ttgtcaggct acaaggtagg ctgcaaaatt aaatctagac attcttttaa tgccaccaca   2253
cgtgttccgc ttctctcttt taaagtattt ataaaaatat aaattgtaca ttttgtaaaa   2313
tattatgttt gatttctcta cttgtcatat cactaaataa acacgatttt attgctgaaa   2373
aaaaaaaaaa aaaaa                                                     2389
```

```
<210> SEQ ID NO 2
<211> LENGTH: 357
<212> TYPE: PRT
<213> ORGANISM: homo sapiens

<400> SEQUENCE: 2

Met Gln Ser Val Gln Ser Thr Ser Phe Cys Leu Arg Lys Gln Cys Leu
1               5                   10                  15

Cys Leu Thr Phe Leu Leu Leu His Leu Leu Gly Gln Val Ala Ala Thr
            20                  25                  30

Gln Arg Cys Pro Pro Gln Cys Pro Gly Arg Cys Pro Ala Thr Pro Pro
        35                  40                  45

Thr Cys Ala Pro Gly Val Arg Ala Val Leu Asp Gly Cys Ser Cys Cys
    50                  55                  60

Leu Val Cys Ala Arg Gln Arg Gly Glu Ser Cys Ser Asp Leu Glu Pro
65                  70                  75                  80

Cys Asp Glu Ser Ser Gly Leu Tyr Cys Asp Arg Ser Ala Asp Pro Ser
                85                  90                  95

Asn Gln Thr Gly Ile Cys Thr Ala Val Glu Gly Asp Asn Cys Val Phe
            100                 105                 110

Asp Gly Val Ile Tyr Arg Ser Gly Glu Lys Phe Gln Pro Ser Cys Lys
        115                 120                 125

Phe Gln Cys Thr Cys Arg Asp Gly Gln Ile Gly Cys Val Pro Arg Cys
    130                 135                 140

Gln Leu Asp Val Leu Leu Pro Glu Pro Asn Cys Pro Ala Pro Arg Lys
145                 150                 155                 160

Val Glu Val Pro Gly Glu Cys Cys Glu Lys Trp Ile Cys Gly Pro Asp
                165                 170                 175

Glu Glu Asp Ser Leu Gly Gly Leu Thr Leu Ala Ala Tyr Arg Pro Glu
            180                 185                 190

Ala Thr Leu Gly Val Glu Val Ser Asp Ser Ser Val Asn Cys Ile Glu
        195                 200                 205

Gln Thr Thr Glu Trp Thr Ala Cys Ser Lys Ser Cys Gly Met Gly Phe
    210                 215                 220

Ser Thr Arg Val Thr Asn Arg Asn Arg Gln Cys Glu Met Leu Lys Gln
225                 230                 235                 240

Thr Arg Leu Cys Met Val Arg Pro Cys Glu Gln Glu Pro Glu Gln Pro
                245                 250                 255

Thr Asp Lys Lys Gly Lys Lys Cys Leu Arg Thr Lys Lys Ser Leu Lys
            260                 265                 270

Ala Ile His Leu Gln Phe Lys Asn Cys Thr Ser Leu His Thr Tyr Lys
```

-continued

```
                    275                 280                 285
Pro Arg Phe Cys Gly Val Cys Ser Asp Gly Arg Cys Cys Thr Pro His
    290                 295                 300

Asn Thr Lys Thr Ile Gln Ala Glu Phe Gln Cys Ser Pro Gly Gln Ile
305                 310                 315                 320

Val Lys Lys Pro Val Met Val Ile Gly Thr Cys Thr Cys His Thr Asn
                325                 330                 335

Cys Pro Lys Asn Asn Glu Ala Phe Leu Gln Glu Leu Glu Leu Lys Thr
                340                 345                 350

Thr Arg Gly Lys Met
        355

<210> SEQ ID NO 3
<211> LENGTH: 216
<212> TYPE: DNA
<213> ORGANISM: Artificial sequence
<220> FEATURE:
<221> NAME/KEY: CDS
<222> LOCATION: (1)..(216)
<220> FEATURE:
<223> OTHER INFORMATION: Description of Artificial Sequence: fragment of
      NOV protein

<400> SEQUENCE: 3 cag cgc tgc cct ccc cag tgc ccg ggc cgg tgc cct gcg acg ccg ccg        48
Gln Arg Cys Pro Pro Gln Cys Pro Gly Arg Cys Pro Ala Thr Pro Pro
1               5                   10                  15 acc tgc gcc ccc ggg gtg cgc gcg gtg ctg gac ggc tgc tca tgc tgt        96
Thr Cys Ala Pro Gly Val Arg Ala Val Leu Asp Gly Cys Ser Cys Cys
            20                  25                  30 ctg gtg tgt gcc cgc cag cgt ggc gag agc tgc tca gat ctg gag cca       144
Leu Val Cys Ala Arg Gln Arg Gly Glu Ser Cys Ser Asp Leu Glu Pro
        35                  40                  45 tgc gac gag agc agt ggc ctc tac tgt gat cgc agc gcg gac ccc agc       192
Cys Asp Glu Ser Ser Gly Leu Tyr Cys Asp Arg Ser Ala Asp Pro Ser
    50                  55                  60 aac cag act ggc atc tgc acg gcg                                        216
Asn Gln Thr Gly Ile Cys Thr Ala
65                  70

<210> SEQ ID NO 4
<211> LENGTH: 72
<212> TYPE: PRT
<213> ORGANISM: artificial sequence
<220> FEATURE:
<223> OTHER INFORMATION: fragment of NOV protein

<400> SEQUENCE: 4

Gln Arg Cys Pro Pro Gln Cys Pro Gly Arg Cys Pro Ala Thr Pro Pro
1               5                   10                  15

Thr Cys Ala Pro Gly Val Arg Ala Val Leu Asp Gly Cys Ser Cys Cys
            20                  25                  30

Leu Val Cys Ala Arg Gln Arg Gly Glu Ser Cys Ser Asp Leu Glu Pro
        35                  40                  45

Cys Asp Glu Ser Ser Gly Leu Tyr Cys Asp Arg Ser Ala Asp Pro Ser
    50                  55                  60

Asn Gln Thr Gly Ile Cys Thr Ala
65                  70

<210> SEQ ID NO 5
<211> LENGTH: 201
```

<212> TYPE: DNA
<213> ORGANISM: artificial sequence
<220> FEATURE:
<221> NAME/KEY: CDS
<222> LOCATION: (1)..(201)
<220> FEATURE:
<223> OTHER INFORMATION: fragment of NOV protein

<400> SEQUENCE: 5

```
gat aac tgt gtg ttc gat ggg gtc atc tac cgc agt gga gag aaa ttt     48
Asp Asn Cys Val Phe Asp Gly Val Ile Tyr Arg Ser Gly Glu Lys Phe
1               5                   10                  15 cag cca agc tgc aaa ttc cag tgc acc tgc aga gat ggg cag att ggc     96
Gln Pro Ser Cys Lys Phe Gln Cys Thr Cys Arg Asp Gly Gln Ile Gly
            20                  25                  30 tgt gtg ccc cgc tgt cag ctg gat gtg cta ctg cct gag cct aac tgc    144
Cys Val Pro Arg Cys Gln Leu Asp Val Leu Leu Pro Glu Pro Asn Cys
        35                  40                  45 cca gct cca aga aaa gtt gag gtg cct gga gag tgc tgt gaa aag tgg    192
Pro Ala Pro Arg Lys Val Glu Val Pro Gly Glu Cys Cys Glu Lys Trp
    50                  55                  60 atc tgt ggc                                                        201
Ile Cys Gly
65
```

<210> SEQ ID NO 6
<211> LENGTH: 67
<212> TYPE: PRT
<213> ORGANISM: artificial sequence
<220> FEATURE:
<223> OTHER INFORMATION: fragment of NOV protein

<400> SEQUENCE: 6

```
Asp Asn Cys Val Phe Asp Gly Val Ile Tyr Arg Ser Gly Glu Lys Phe
1               5                   10                  15

Gln Pro Ser Cys Lys Phe Gln Cys Thr Cys Arg Asp Gly Gln Ile Gly
            20                  25                  30

Cys Val Pro Arg Cys Gln Leu Asp Val Leu Leu Pro Glu Pro Asn Cys
        35                  40                  45

Pro Ala Pro Arg Lys Val Glu Val Pro Gly Glu Cys Cys Glu Lys Trp
    50                  55                  60

Ile Cys Gly
65
```

<210> SEQ ID NO 7
<211> LENGTH: 135
<212> TYPE: DNA
<213> ORGANISM: artificial sequence
<220> FEATURE:
<221> NAME/KEY: CDS
<222> LOCATION: (1)..(135)
<220> FEATURE:
<223> OTHER INFORMATION: fragment of NOV protein

<400> SEQUENCE: 7

```
tgc att gaa cag acc aca gag tgg aca gca tgc tcc aag agc tgt ggt     48
Cys Ile Glu Gln Thr Thr Glu Trp Thr Ala Cys Ser Lys Ser Cys Gly
1               5                   10                  15 atg ggg ttc tcc acc cgg gtc acc aat agg aac cgt caa tgt gag atg     96
Met Gly Phe Ser Thr Arg Val Thr Asn Arg Asn Arg Gln Cys Glu Met
            20                  25                  30 ctg aaa cag act cgg ctc tgc atg gtg cgg ccc tgt gaa                135
Leu Lys Gln Thr Arg Leu Cys Met Val Arg Pro Cys Glu
        35                  40                  45
```

<210> SEQ ID NO 8
<211> LENGTH: 45
<212> TYPE: PRT
<213> ORGANISM: artificial sequence
<220> FEATURE:
<223> OTHER INFORMATION: fragment of NOV protein

<400> SEQUENCE: 8

Cys Ile Glu Gln Thr Thr Glu Trp Thr Ala Cys Ser Lys Ser Cys Gly
1               5                  10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu
        35                  40                  45

<210> SEQ ID NO 9
<211> LENGTH: 225
<212> TYPE: DNA
<213> ORGANISM: artificial sequence
<220> FEATURE:
<221> NAME/KEY: CDS
<222> LOCATION: (1)..(225)
<220> FEATURE:
<223> OTHER INFORMATION: fragment of NOV protein

<400> SEQUENCE: 9 tgt ctc cgc acc aag aag tca ctc aaa gcc atc cac ctg cag ttc aag      48
Cys Leu Arg Thr Lys Lys Ser Leu Lys Ala Ile His Leu Gln Phe Lys
1               5                  10                  15 aac tgc acc agc ctg cac acc tac aag ccc agg ttc tgt ggg gtc tgc      96
Asn Cys Thr Ser Leu His Thr Tyr Lys Pro Arg Phe Cys Gly Val Cys
            20                  25                  30 agt gat ggc cgc tgc tgc act ccc cac aat acc aaa acc atc cag gca     144
Ser Asp Gly Arg Cys Cys Thr Pro His Asn Thr Lys Thr Ile Gln Ala
        35                  40                  45 gag ttt cag tgc tcc cca ggg caa ata gtc aag aag cca gtg atg gtc     192
Glu Phe Gln Cys Ser Pro Gly Gln Ile Val Lys Lys Pro Val Met Val
    50                  55                  60 att ggg acc tgc acc tgt cac acc aac tgt cct                         225
Ile Gly Thr Cys Thr Cys His Thr Asn Cys Pro
65                  70                  75

<210> SEQ ID NO 10
<211> LENGTH: 75
<212> TYPE: PRT
<213> ORGANISM: artificial sequence
<220> FEATURE:
<223> OTHER INFORMATION: fragment of NOV protein

<400> SEQUENCE: 10

Cys Leu Arg Thr Lys Lys Ser Leu Lys Ala Ile His Leu Gln Phe Lys
1               5                  10                  15

Asn Cys Thr Ser Leu His Thr Tyr Lys Pro Arg Phe Cys Gly Val Cys
            20                  25                  30

Ser Asp Gly Arg Cys Cys Thr Pro His Asn Thr Lys Thr Ile Gln Ala
        35                  40                  45

Glu Phe Gln Cys Ser Pro Gly Gln Ile Val Lys Lys Pro Val Met Val
    50                  55                  60

Ile Gly Thr Cys Thr Cys His Thr Asn Cys Pro
65                  70                  75

-continued

```
<210> SEQ ID NO 11
<211> LENGTH: 510
<212> TYPE: DNA
<213> ORGANISM: Homo sapiens
<220> FEATURE:
<221> NAME/KEY: CDS
<222> LOCATION: (1)..(510)

<400> SEQUENCE: 11 gct tac agg cca gaa gcc acc cta gga gta gaa gtc tct gac tca agt      48
Ala Tyr Arg Pro Glu Ala Thr Leu Gly Val Glu Val Ser Asp Ser Ser
1               5                   10                  15 gtc aac tgc att gaa cag acc aca gag tgg aca gca tgc tcc aag agc      96
Val Asn Cys Ile Glu Gln Thr Thr Glu Trp Thr Ala Cys Ser Lys Ser
                20                  25                  30 tgt ggt atg ggg ttc tcc acc cgg gtc acc aat agg aac cgt caa tgt     144
Cys Gly Met Gly Phe Ser Thr Arg Val Thr Asn Arg Asn Arg Gln Cys
            35                  40                  45 gag atg ctg aaa cag act cgg ctc tgc atg gtg cgg ccc tgt gaa caa     192
Glu Met Leu Lys Gln Thr Arg Leu Cys Met Val Arg Pro Cys Glu Gln
        50                  55                  60 gag cca gag cag cca aca gat aag aaa gga aaa aag tgt ctc cgc acc     240
Glu Pro Glu Gln Pro Thr Asp Lys Lys Gly Lys Lys Cys Leu Arg Thr
65                  70                  75                  80 aag aag tca ctc aaa gcc atc cac ctg cag ttc aag aac tgc acc agc     288
Lys Lys Ser Leu Lys Ala Ile His Leu Gln Phe Lys Asn Cys Thr Ser
                85                  90                  95 ctg cac acc tac aag ccc agg ttc tgt ggg gtc tgc agt gat ggc cgc     336
Leu His Thr Tyr Lys Pro Arg Phe Cys Gly Val Cys Ser Asp Gly Arg
                100                 105                 110 tgc tgc act ccc cac aat acc aaa acc atc cag gca gag ttt cag tgc     384
Cys Cys Thr Pro His Asn Thr Lys Thr Ile Gln Ala Glu Phe Gln Cys
            115                 120                 125 tcc cca ggg caa ata gtc aag aag cca gtg atg gtc att ggg acc tgc     432
Ser Pro Gly Gln Ile Val Lys Lys Pro Val Met Val Ile Gly Thr Cys
        130                 135                 140 acc tgt cac acc aac tgt cct aag aac aat gag gcc ttc ctc cag gag     480
Thr Cys His Thr Asn Cys Pro Lys Asn Asn Glu Ala Phe Leu Gln Glu
145                 150                 155                 160 ctg gag ctg aag act acc aga ggg aaa atg                             510
Leu Glu Leu Lys Thr Thr Arg Gly Lys Met
                165                 170

<210> SEQ ID NO 12
<211> LENGTH: 170
<212> TYPE: PRT
<213> ORGANISM: Homo sapiens

<400> SEQUENCE: 12

Ala Tyr Arg Pro Glu Ala Thr Leu Gly Val Glu Val Ser Asp Ser Ser
1               5                   10                  15

Val Asn Cys Ile Glu Gln Thr Thr Glu Trp Thr Ala Cys Ser Lys Ser
                20                  25                  30

Cys Gly Met Gly Phe Ser Thr Arg Val Thr Asn Arg Asn Arg Gln Cys
            35                  40                  45

Glu Met Leu Lys Gln Thr Arg Leu Cys Met Val Arg Pro Cys Glu Gln
        50                  55                  60

Glu Pro Glu Gln Pro Thr Asp Lys Lys Gly Lys Lys Cys Leu Arg Thr
65                  70                  75                  80

Lys Lys Ser Leu Lys Ala Ile His Leu Gln Phe Lys Asn Cys Thr Ser
                85                  90                  95
```

-continued

```
Leu His Thr Tyr Lys Pro Arg Phe Cys Gly Val Cys Ser Asp Gly Arg
            100             105             110

Cys Cys Thr Pro His Asn Thr Lys Thr Ile Gln Ala Glu Phe Gln Cys
        115             120             125

Ser Pro Gly Gln Ile Val Lys Lys Pro Val Met Val Ile Gly Thr Cys
        130             135             140

Thr Cys His Thr Asn Cys Pro Lys Asn Asn Glu Ala Phe Leu Gln Glu
145             150             155             160

Leu Glu Leu Lys Thr Thr Arg Gly Lys Met
                165             170
```